United States Patent
Katzmark

(10) Patent No.: US 12,397,255 B2
(45) Date of Patent: Aug. 26, 2025

(54) AIR FILTRATION SYSTEM

(71) Applicant: PMK Products, LLC, North Haven, CT (US)

(72) Inventor: Michael Katzmark, Bethany, CT (US)

(73) Assignee: PMK PRODUCTS, LLC, North Haven, CT (US)

( * ) Notice: Subject to any disclaimer, the term of this patent is extended or adjusted under 35 U.S.C. 154(b) by 606 days.

(21) Appl. No.: 17/553,913

(22) Filed: Dec. 17, 2021

(65) Prior Publication Data

US 2022/0203284 A1   Jun. 30, 2022

Related U.S. Application Data

(60) Provisional application No. 63/126,642, filed on Dec. 17, 2020.

(51) Int. Cl.
*B01D 46/00* (2022.01)
*A61L 9/20* (2006.01)
(Continued)

(52) U.S. Cl.
CPC ............ *B01D 46/0028* (2013.01); *A61L 9/20* (2013.01); *B01D 46/001* (2013.01);
(Continued)

(58) Field of Classification Search
CPC ...... F24F 3/16; F24F 8/10; F24F 11/89; F24F 13/28; F24F 13/0272; F24F 13/0236;
(Continued)

(56) References Cited

U.S. PATENT DOCUMENTS 4,334,899 A * 6/1982 McConnell ............ B01D 50/20
55/DIG. 35
5,558,158 A * 9/1996 Elmore ..................... A61L 9/20
165/122

(Continued)

FOREIGN PATENT DOCUMENTS

CN 106839116 A 6/2017
CN 109210634 A 1/2019
(Continued)

OTHER PUBLICATIONS

UVGI Return Air Grill System, nelbud.com, accessed Oct. 7, 2020, https://www.nelbud.com/shop/uvgi-return-air-grill-system, 5 pages.
(Continued)

*Primary Examiner* — Jennifer Dieterle
*Assistant Examiner* — Sonji Turner
(74) *Attorney, Agent, or Firm* — Ware, Fressola, Maguire & Barber LLP

(57) ABSTRACT

An air filtration system comprising an extrusion frame with an associated grille proximal to an occupied space, the frame dimension for insertion within a drop ceiling or solid ceiling associated with either a plenum air space or directly to a return air duct associated with an air handler and conditioned supply air, a pleated filter positioned adjacent the grille so as to filter air flowing into the plenum air space from the occupied space, the pleated filter dimensioned for entrapping particles in the 1 to 3 micron size, an ultraviolet lamp for emitting UV-C light positioned adjacent the pleated air filter so as to substantially irradiate airborne particles that may pass through the pleated filter and, in particular to irradiate particles associated with microorganisms, including viruses, an electrical switch and associated electrical ballast for controlling operation of the electrical lamp and so as to ensure that the lamp is not energized when the air filtration system is being installed or service; and means for (Continued)

securing the extruded frame of the air filtration system to a drop ceiling or solid ceiling or wall.

12 Claims, 15 Drawing Sheets

(51) Int. Cl.
  *B01D 46/42* (2006.01)
  *B01D 46/52* (2006.01)
  *F24F 8/108* (2021.01)
  *F24F 8/175* (2021.01)
  *F24F 13/28* (2006.01)

(52) U.S. Cl.
  CPC ....... *B01D 46/4245* (2013.01); *B01D 46/521* (2013.01); *F24F 8/108* (2021.01); *F24F 8/175* (2021.01); *F24F 13/28* (2013.01); *A61L 2209/14* (2013.01); *A61L 2209/15* (2013.01); *B01D 2279/35* (2013.01); *B01D 2279/50* (2013.01); *B01D 2279/65* (2013.01)

(58) Field of Classification Search
  CPC .... F24F 13/02; F24F 13/0209; F24F 13/0218; F24F 13/0227; F24F 13/0245; F24F 13/0254; F24F 13/0263; F24F 13/0281; F24F 13/029; F24F 13/04; F24F 13/06; F24F 13/068; F24F 13/072; F24F 13/20; F24F 2013/205; F24F 2013/202; F24F 2013/0616
  See application file for complete search history.

(56) References Cited

U.S. PATENT DOCUMENTS

| | | | |
|---|---|---|---|
| 6,063,170 A | 5/2000 | Deibert | |
| 6,193,603 B1 | 2/2001 | Tai | |
| 6,224,655 B1 * | 5/2001 | Messier | B01D 46/0028 55/497 |
| 6,500,267 B1 | 12/2002 | Fencl et al. | |
| 6,653,647 B1 | 11/2003 | Vilarasau Alegre | |
| 6,849,107 B1 | 2/2005 | Huffman | |
| 7,763,212 B2 | 7/2010 | McEllen | |
| 8,038,949 B2 | 10/2011 | Horne et al. | |
| 8,328,917 B2 | 12/2012 | Garfield et al. | |
| 8,350,228 B2 | 1/2013 | Welker | |
| 9,283,295 B2 * | 3/2016 | Fink | A61L 9/20 |
| 9,339,579 B2 | 5/2016 | Willette | |
| 9,498,555 B2 | 11/2016 | Hingorani et al. | |
| 9,737,842 B2 * | 8/2017 | Matlin | F24F 8/158 |
| 10,753,626 B2 * | 8/2020 | Skelton | F24F 8/22 |
| 2006/0000360 A1 | 1/2006 | Shou et al. | |
| 2009/0056539 A1 | 3/2009 | Garrett | |
| 2009/0133582 A1 | 5/2009 | Snowball | |
| 2013/0189162 A1 | 7/2013 | Jeong | |
| 2015/0306269 A1 | 10/2015 | Bullard et al. | |
| 2018/0147312 A1 | 5/2018 | Ryerson | |
| 2019/0292315 A1 * | 9/2019 | Niemiec | E04B 9/02 |
| 2020/0289698 A1 * | 9/2020 | Polidoro | F21S 8/04 |
| 2020/0297890 A1 | 9/2020 | Skelton et al. | |

FOREIGN PATENT DOCUMENTS

| | | |
|---|---|---|
| CN | 106500208 B | 6/2019 |
| ES | 2169007 B1 | 4/2003 |
| WO | 2005056064 A1 | 6/2005 |

OTHER PUBLICATIONS

Healthy Climate and Germicidal Light, lennoxpros.com, accessed Oct. 7, 2020, 13 pages.
In-Duct (Air Stream) Germicidal UV Light—2 Lamps (DC), uvlightsolutions.com, accessed Oct. 7, 2020, 6 pages.
Bruls et al., Photochem Photobiol. 1984;40:485-94.
American Conference of Governmental Industrial Hygienists. TLVs and BEIs. Cincinnati: ACGIH; 1999.
International Commission on Non-Ionizing Radiation Protection. Guidelines on UV radiation exposure limits, Health Phys. 1996;71:978.
Illuminating Engineering Society of North America. RP-27.2-00. IESNA Photobiology Committee. Recommended practice for photobiological safety for lamps and lamp systems-measurement systems, techniques. New York: IESNA, 2000.
Trevisan, et al., Unusual high exposure to ultraviolet-C radiation. Photochem Photobiol. 2006;82:1077-9.
First et al., Monitoring human exposures to upper-room germicidal ultraviolet irradiation. J Occup Environ Hyg. 2005;2:285-92.
Brickner et al., The application of ultraviolet germicidal irradiation to control transmission of airborne disease: Bioterrorism countermeasure. Public Health Report 118(2):99-114. 2003.
Comprehensive procedures for collecting environmental samples for culturing Bacillus anthracis. Centers for Disease Control and Prevention, Atlanta. www.cdc.gov/niosh/topics/emres/unp-envsamp.html. CDC. 2005.
Guidelines for preventing the transmission of *Mycobacterium tuberculosis* in health-care settings. Morbidity and Mortality Weekly Report (MMWR) 37-38, 70-75. 2005.
McDevitt et al., Inactivation of poxviruses by upper-room UV-C light in a simulated hospital room environment. PLoS ONE3(9):e3186. journals.plos.org/plosone/article?id=10.1371/journal.pone.0003186. 2008.

* cited by examiner

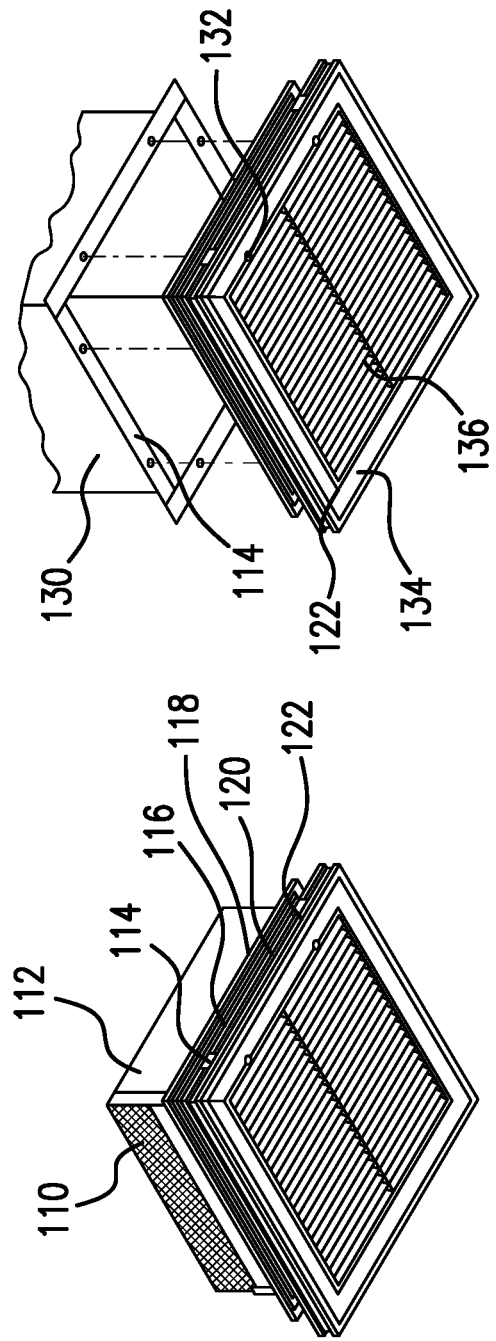

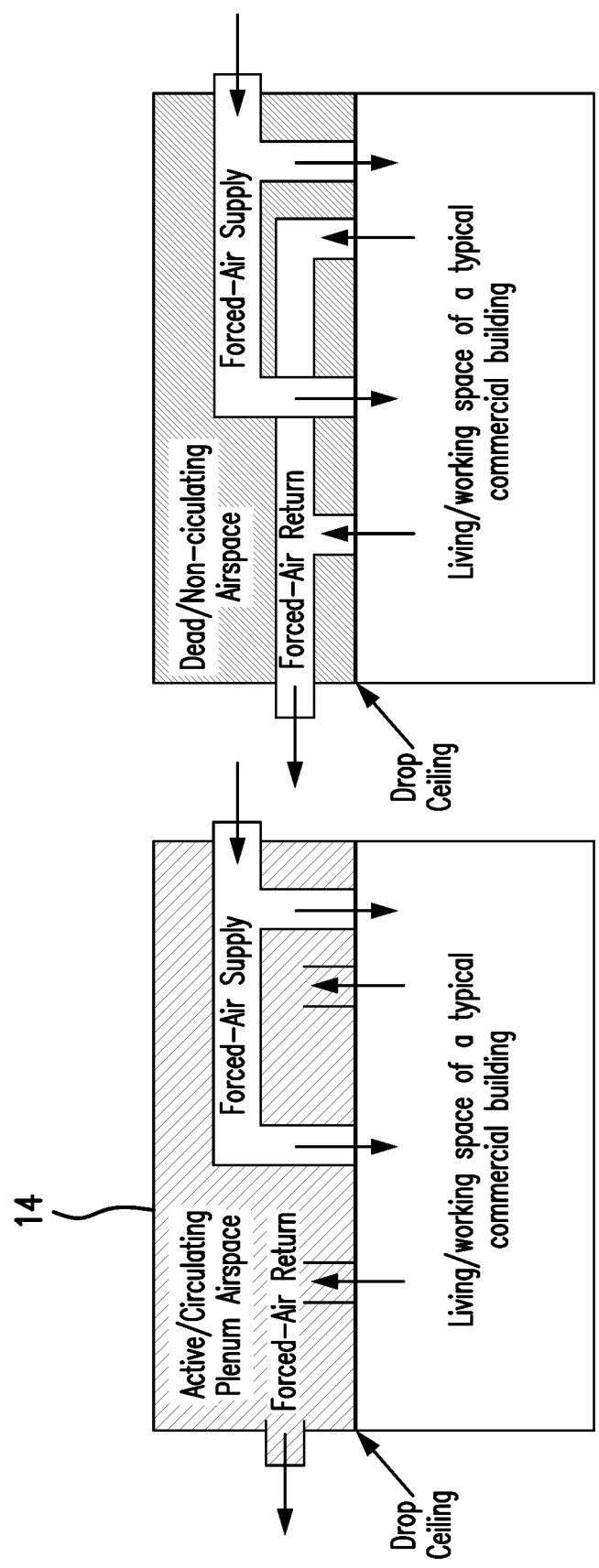

AIR FILTRATION SYSTEM

TECHNICAL FIELD

The present invention is an air filtration system, in particular, a room return air-filtration system with UV-C air purification. This system filters and cleans the air as it exits the conditioned space/occupied space and prior to entering the return air plenum to increase occupant safety and aid delivering cleaner air back into the occupied space. This ensures the air stream entering from multiple conditioned spaces does not become cross contaminated, effectively isolating each conditioned space/occupied space and the return air plenum, with the air handling system thus being supplied into the conditioned space/occupied space. The system may comprise a universal drop-in flanged frame, grille with filter access, filter, deflector plate, extruded aluminum screen reflector, UV-C germicidal chamber, UV-C germicidal lamp, duct flange and upper diffuser screen.

SUMMARY OF THE INVENTION

The object of the invention is to provide an air filtration system in solid or gridded drop ceiling panel system that will clean the air prior to leaving the conditioned space/occupied space. The filter system is designed so it can be installed in both ducted and open plenum ceiling returns, in both new construction and as a retrofit in currently occupied spaces. The pleated particulate air filter and UV-C germicidal lamp are serviceable/replaceable without disassembly, and can safely be serviced without tools. The air filtration system can be accessed from the conditioned space/occupied space, without having to enter the return air plenum. It is designed to allow easy cleaning and maintenance of louvers, lamp, and reflectors.

The filter and UV-C lamp of the system are arranged so filtration and air cleaning removes the unwanted material, including airborne particulates, human generated respiratory droplets and droplet nuclei (dried respiratory droplets) that are predominantly 1 μm in size and larger as well as on-the-fly inactivation of microorganisms from entering the return air stream.

The air filtration system has a pleated particulate air filter that keeps the filter face velocity and the media velocity roughly the same, while the increased surface area of the pleated filter reduces the velocity of the airflow through the filter media, allowing increased collection efficiency. The particulate filter collects the particles in three ways; impaction which occurs when a particle travels in the air stream and passes around a filter fiber, and deviates from the air stream (due to particle inertia) and collides with a fiber; interception, which occurs when a large particle, because of its size, collides with a fiber in the filter that the air stream is passing through; and diffusion, which occurs when the random (Brownian) motion of a particle causes that particle to contact a fiber. The filter is rated at MERV-13 and has been tested to remove capturing particles in 1 μm to 3 μm size range. This capture is at least 85% efficient.

A germicidal ultraviolet lamp enclosed, within a germicidal irradiation chamber, is used as an additional engineering control to interrupt the transmission of pathogenic microorganisms. The design and placement is integral to the system and the location of the fixture allows for the highest possible dose rate due to it being at the point where the filtered air leaves the conditioned space/occupied space. This is the point where the air velocity and volume within the system are at their lowest and therefore provides the highest possible UV dose rate within the system. The usefulness of UV-C irradiation on air quality lies in its affect on microorganisms/germs transmitted in aerosolized form. Microorganisms are generally less than 0.3 microns in diameter and are suspended or "float" in the air and if they pass through the pleated particulate air filter, they encounter the UV-C radiation, resulting in a reduction in the total number of viable pathogenic microorganisms (greatly reduced in an airstream allowing for near 360° global exposure, leading to UV-C energy absorption of a sufficient amount. Note: testing via Intrek to set "Time").

The placement of the system is within the room where the airborne particulates, human generated respiratory droplets and droplet nuclei originate. The arrangement of the components from the conditioned space/occupied space to the return air plenum avoids UV-C radiation in the lower part of a room, i.e. the part of the room populated by people, well below the height at which the UV-C lamps of the system are located. In an embodiment of the invention, the air moves from the space at a maximum velocity of 400-1000 cubic feet per minute and passes into a typical 24 inch by 24 or 48 inch extruded aluminum frame with duct mounting holes, and through a 20 inch by 20 or 40 inch fixed bar grille, into the pleated MERV-13 filter removing particles and blocking the UV-C radiation from being projected into the room, and over the UV-C lamp located in the upper portion of the frame and then exiting into the return plenum through the upper diffuser screen.

The UV-C lamping uses germicidal fluorescent bulbs that are permanently connected at the base and have end connectors that plug into a pair of interconnected sockets. The "germicidal" UV wavelength is typically 253.7 nm. The UV-C lamps are typically treated with an interior coating that prevents any vacuum UV (that is, 200 nm and below) from being emitted from the lamp and eliminates ozone production.

The operation of the air filtration system according to the present invention can be performed from within the room by, for example, hard-wired switches, occupancy sensors, that control the air filtration system or by a remote control system and is determined by the installer, project engineer and/or the owner. The air filtration system contains a safety switch, which will interrupt the power to the UV-C germicidal lamp upon opening of the grille to ensure worker safety.

DESCRIPTION OF DRAWINGS

FIG. 12 is another perspective view of the air filtration system for a plenum installation.

FIG. 13 is another perspective view of the air filtration system for a ducted return installation, showing the duct partially cut away.

FIG. 14 is a diagrammatic view of a plenum airspace associated with a drop ceiling.

FIG. 15 is a diagrammatic view of a non-circulating airspace associated with a drop ceiling.

DETAILED DESCRIPTION

Figure 1A:
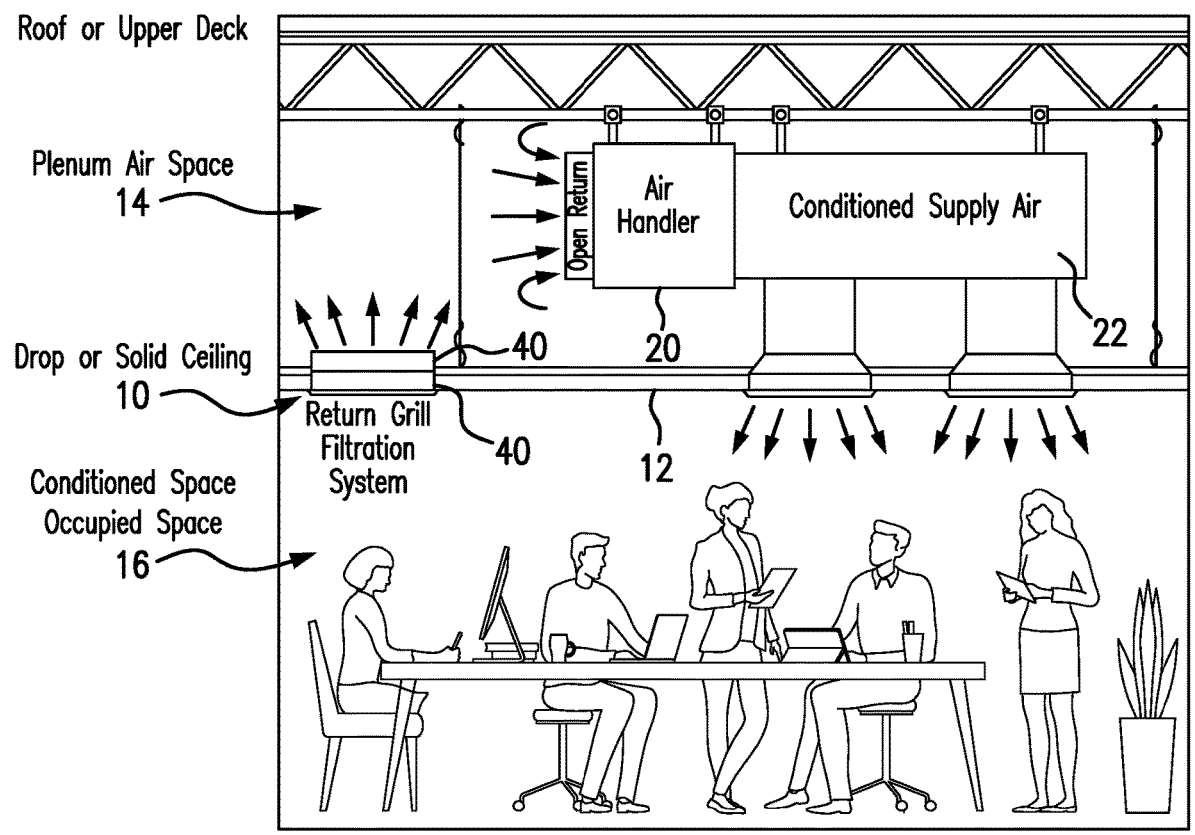
FIGS. 1A and 1B are sectional views in a drop ceiling of an air filtration system according to an embodiment of the present invention. These figures illustrate a grid system with the air filtration system in the plenum or in a duct.

FIG. 1A shows a plan view in a drop ceiling having an air filtration system 10 according to an embodiment of the present invention. This view shows where the air filtration system is in a drop ceiling 12 and communicates directly into the plenum air space 14 associated with an occupied space 16.

Figure 1B:
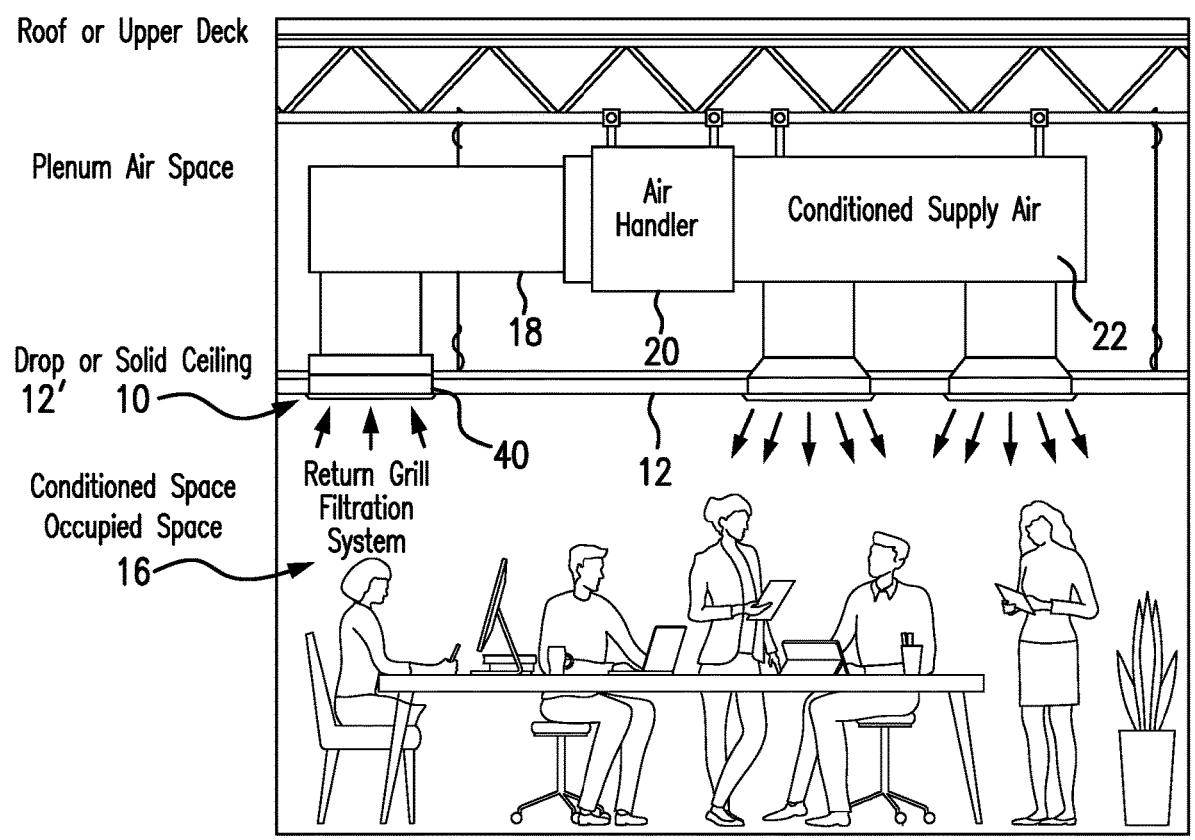

FIG. 1B shows an embodiment of the air filtration system 10 directly interfaced with a drop of solid ceiling 12' and directly communicating with a return air plenum directly connected with an air handler 20 and then to a conditioned supply air space 22 associated with the occupied space 16.

Figure 2:
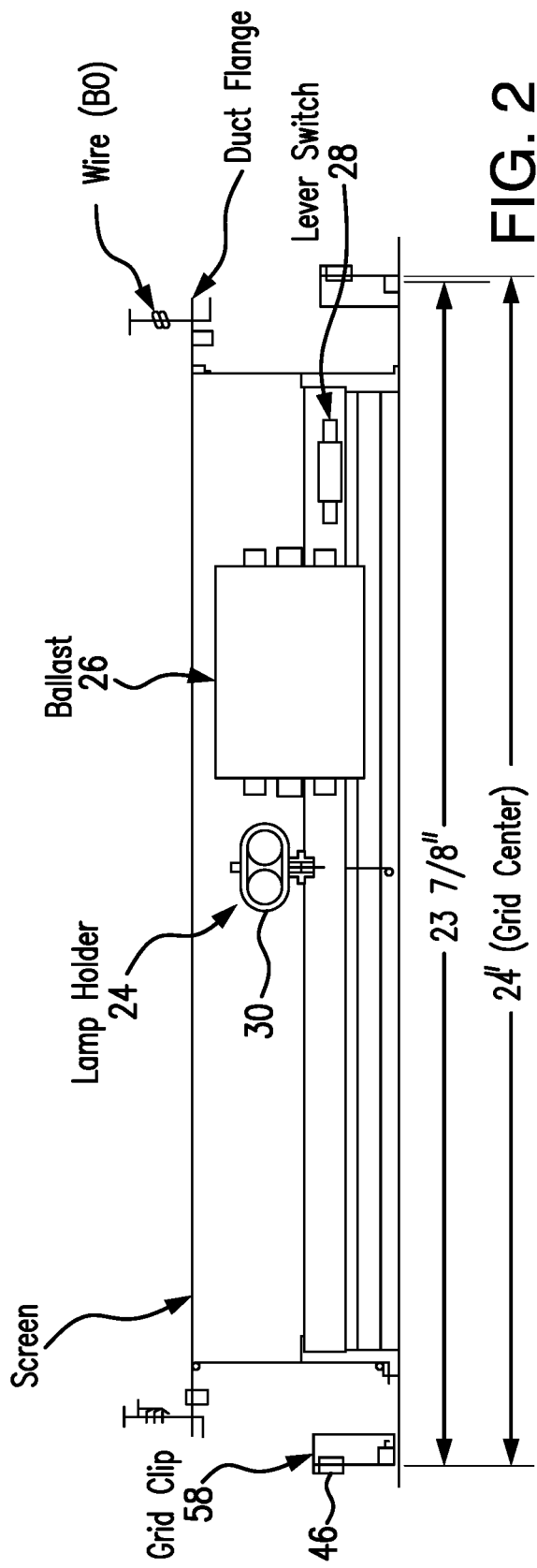
FIG. 2 is a side view of the electrical components of the air filtration system 10.

FIG. 2 is a side view of the electrical components of the air filtration system 10. As seen there, the electrical components include a lamp holder 24, an electrical ballast 26, a lever switch 28 and UV-C lamps 30. The system 10 is secured to ceiling grid clips 58 by means of flat grid preludes 42, grid interludes 44, grid silhouettes 46 and grid superfines 48 as best since in FIG. 6.

Figure 3:
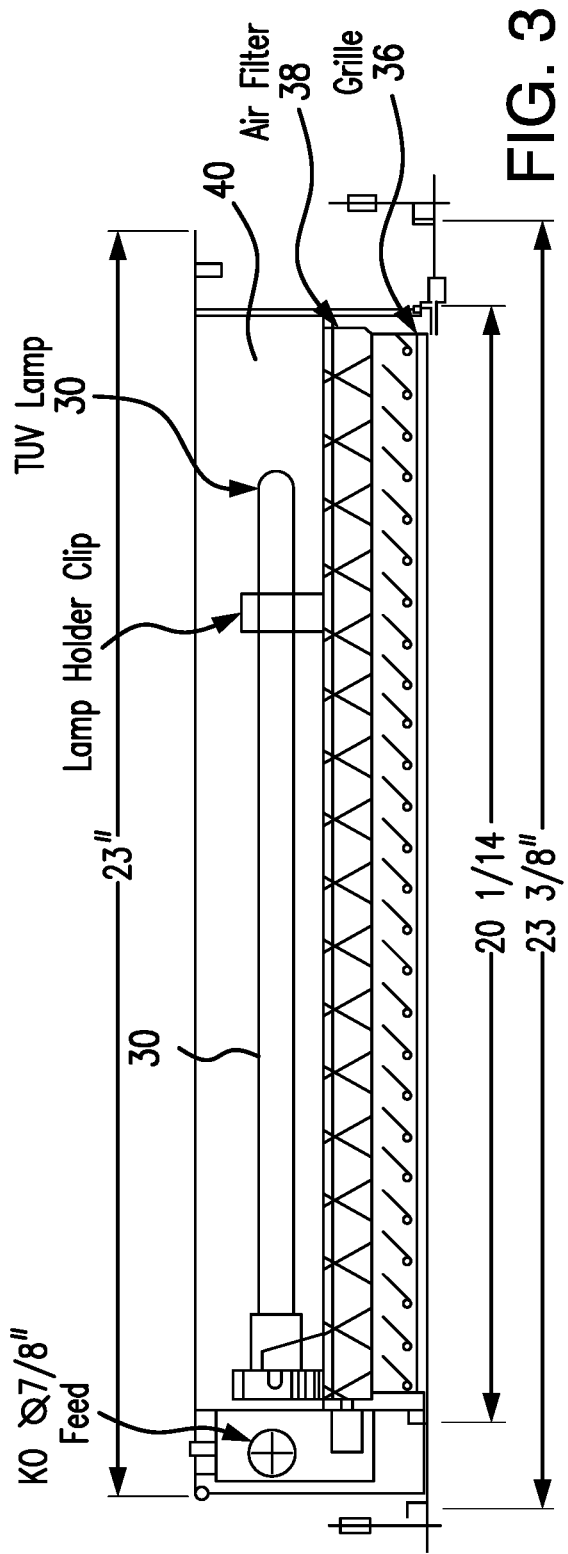
FIG. 3 is a right side cross-section/cut away view of the air filtration system

FIG. 3 shows a right side cross-sectional view of the air filtration system.

In addition, FIG. 3 shows an air filter 38 positioned between the grille 36 and the UV-C lamp 30.

Figure 4:
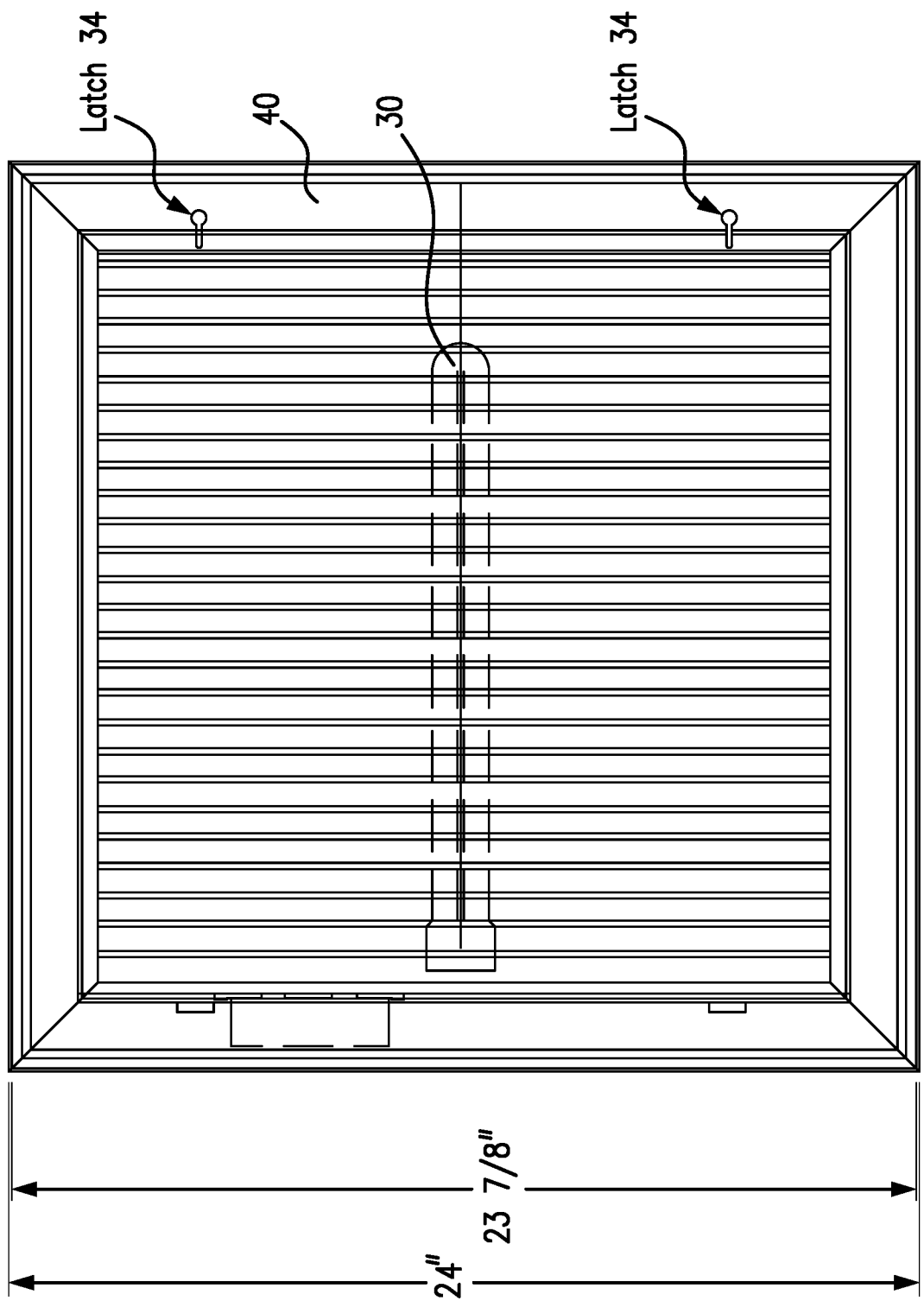
FIG. 4 is a bottom view of the air filtration system.

FIG. 4 shows a bottom view of the air filtration system including a reflector plate 32, latches 34, and grille 36.

Figure 5:
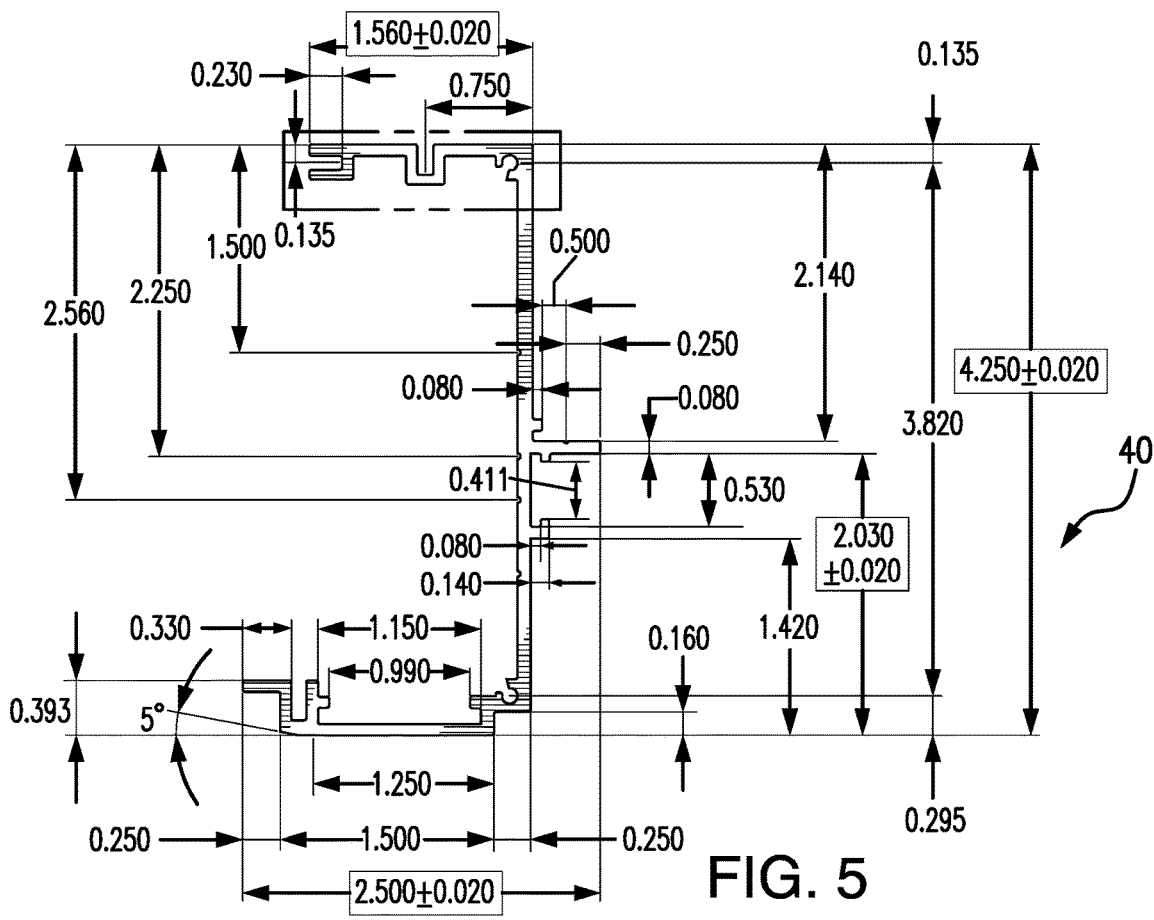
FIG. 5 illustrates a one-piece extrusion cross-section of an embodiment of the air filtration system.

FIG. 5 illustrates details of a one-piece extrusion cross-section 40 used to construct the extrusion frame of the air filtration system.

Figure 6:
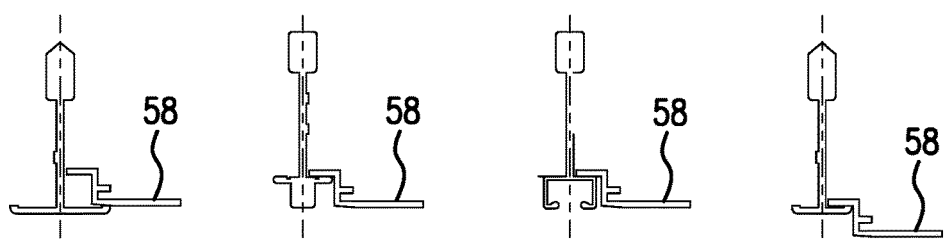
FIG. 6 illustrates a cross-section ceiling mount option for the air filtration system.

FIG. 6 illustrates in cross-section various ceiling mounting options for the air filtration system including flat grid preludes 42, grid interludes 44, grid silhouettes 46 and grid superfines 48, all of which interface with ceiling grid clips 58.

Figure 7:
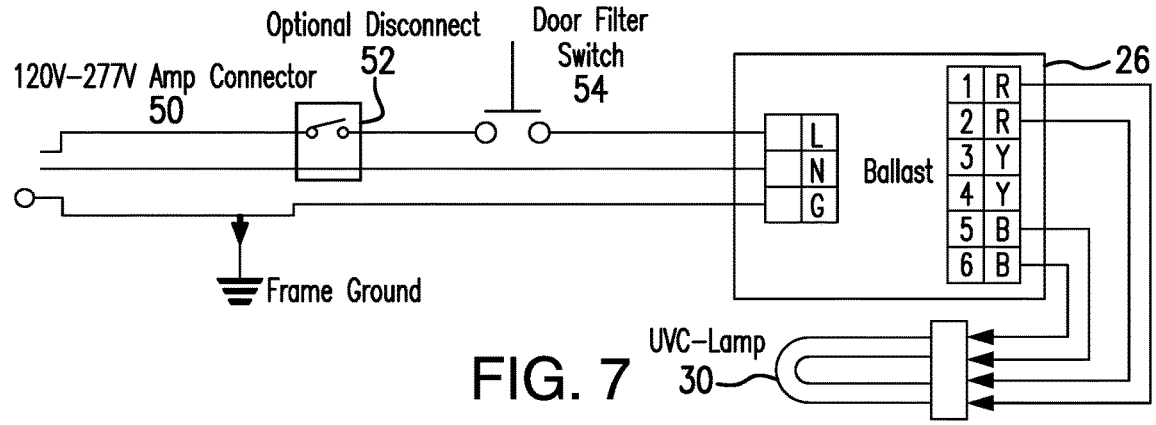
FIG. 7 is a schematic diagram of the electrical wiring of the air filtration system.

FIG. 7 is an electrical schematic diagram of the electrical wiring of the air filtration system including a 120V-277V Amp connector 50, an optional disconnect switch 52, a door filter switch 54, ballast 26 and UV-C lamp 30.

Figure 8:
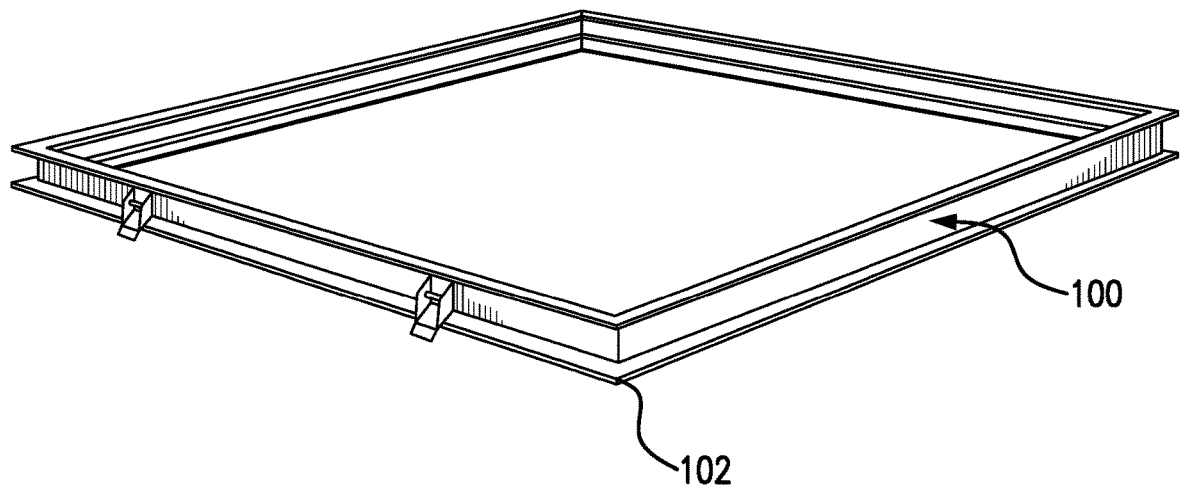
FIG. 8 is a perspective view of a recessed mounting kit for drywall ceilings.
Figure 9:
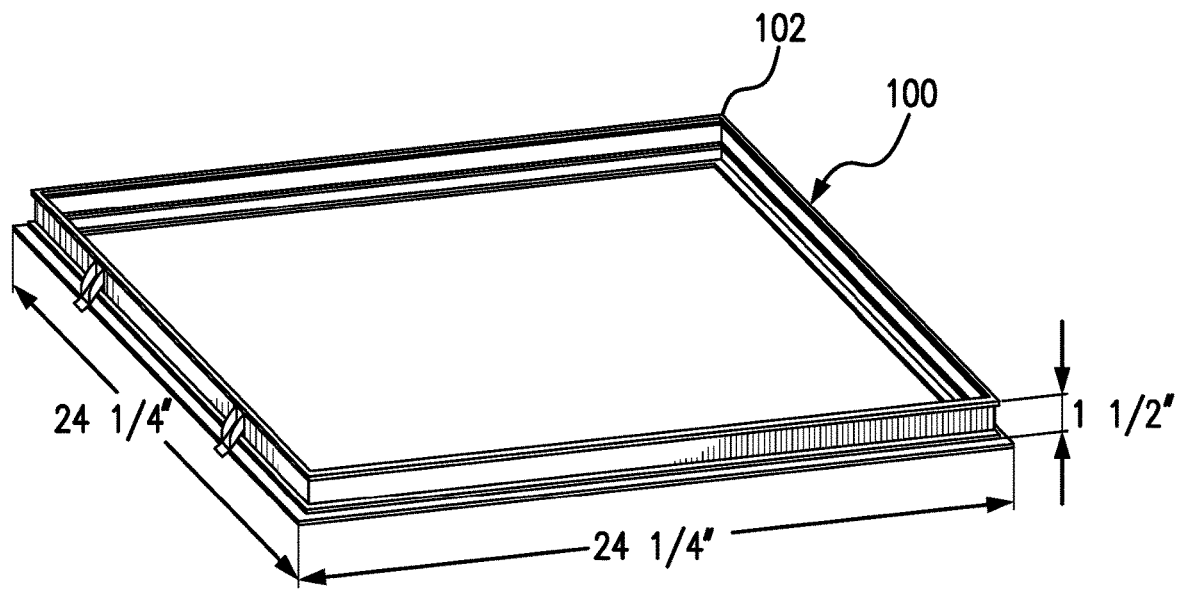
FIG. 9 is a perspective view of the recessed mounting kit shown in FIG. 8, including typical dimensions.

FIGS. 8 and 9 are perspective views of a recessed mounting kit 100 for use in installing the air filtration system 10 into drywall ceilings or walls of a building. The recessed mounting kit 100 may be constructed from extruded aluminum. It may have mitered corners 102 so as to obtain a square fit.

Figure 10:
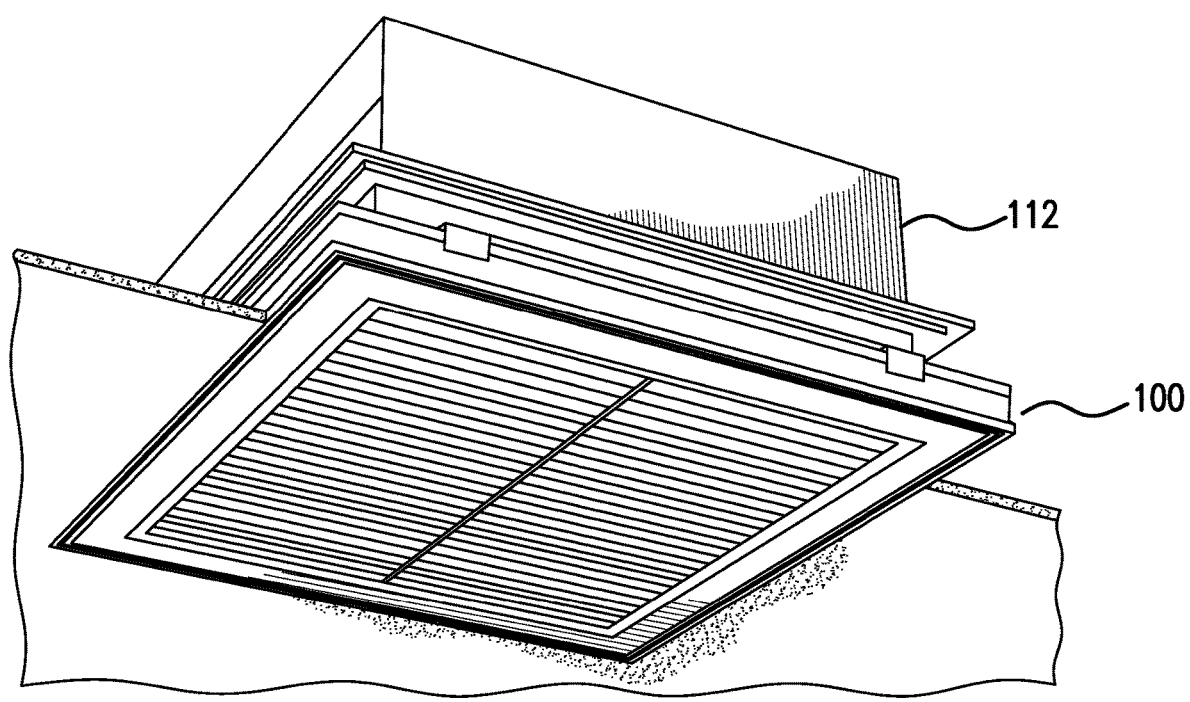
FIG. 10 is a perspective view of the air filtration system for a plenum installation.
Figure 11:
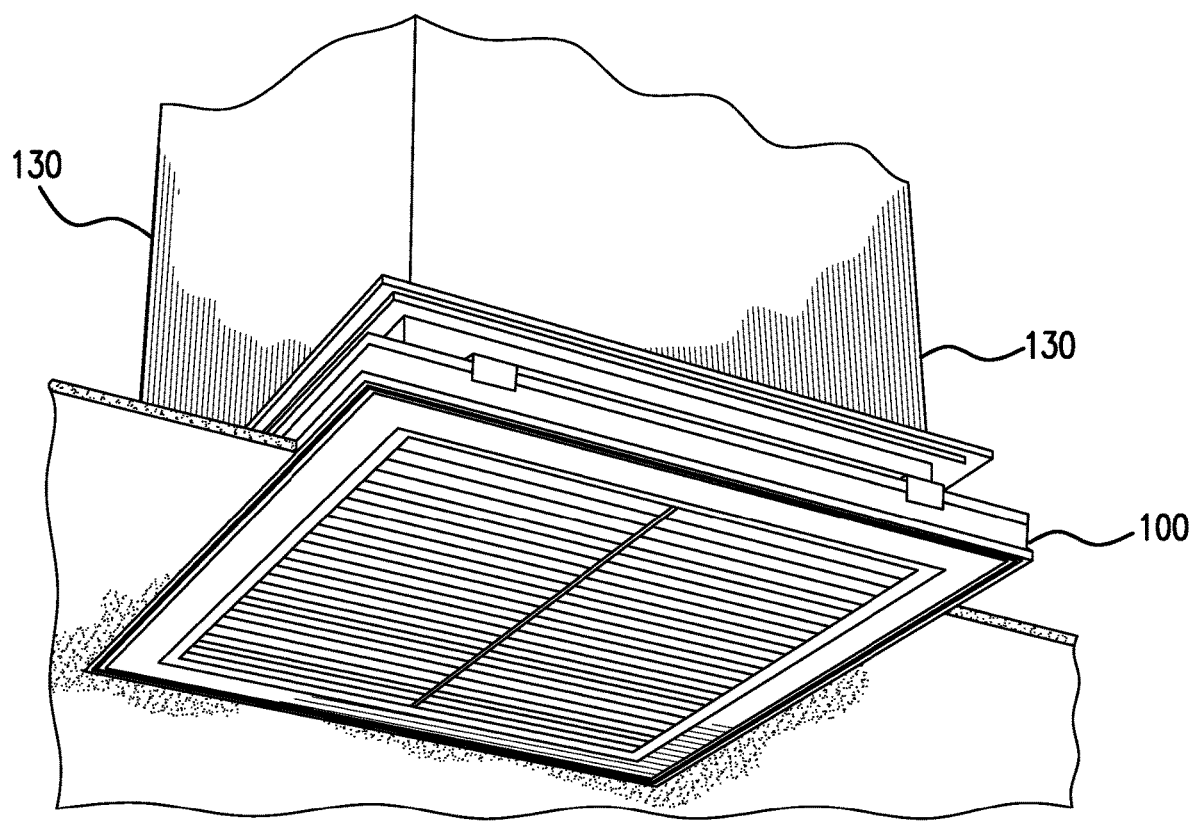
FIG. 11 is a perspective view of the air filtration system for a ducted return installation, showing the duct partially cut away.

FIGS. 10 and 11 show plenum and ducted mounting of the air filtration system to a solid ceiling or wall of a building.

FIGS. 10 and 11 show a recessed mounting kit 100 where the air filtration system 10 sits or is nested to the mounting kit. Once the mounting kit is installed, it allows the air filtration system to be installed and/or removed without the need for additional cutting or patching of the ceiling or finished wall.

As also shown in FIGS. 1A and 1B, a plenum 14 is the open space between the roof or floor above and the ceiling of the room and to return air back to the heating and/or cooling unit associated with the room. A ducted return returns the air but does not also mix the air above the ceiling. This feature is shown in FIGS. 14 and 15.

FIGS. 11 and 12 respectively illustrate a plenum installation and a ducted return installation of the air filtration system.

FIGS. 12 and 13 respectively illustrate a plenum installation and a ducted return installation of the air filtration system.

The parts shown are identified below:

FIG. 12 reflector mesh diffuser 110 vent plenum cover 112 mounting hardware 114 grid brackets 116 fixture upper flange 118 housing assembly 120 ceiling grid 122

FIG. 13 air return duct 130 mounting hardware 114 turn button lock 132 housing assembly 134 air grille 136

Figure 16:
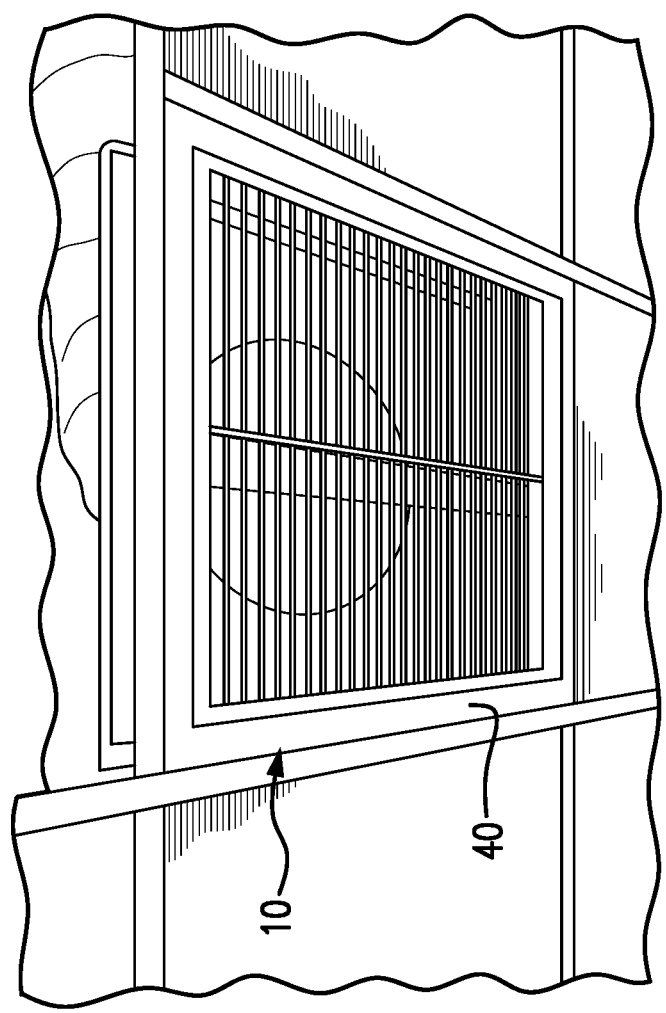
FIGS. 16 and 17 show the air filtration system 10 mounted in the return air space of a drop ceiling.
Figure 17:
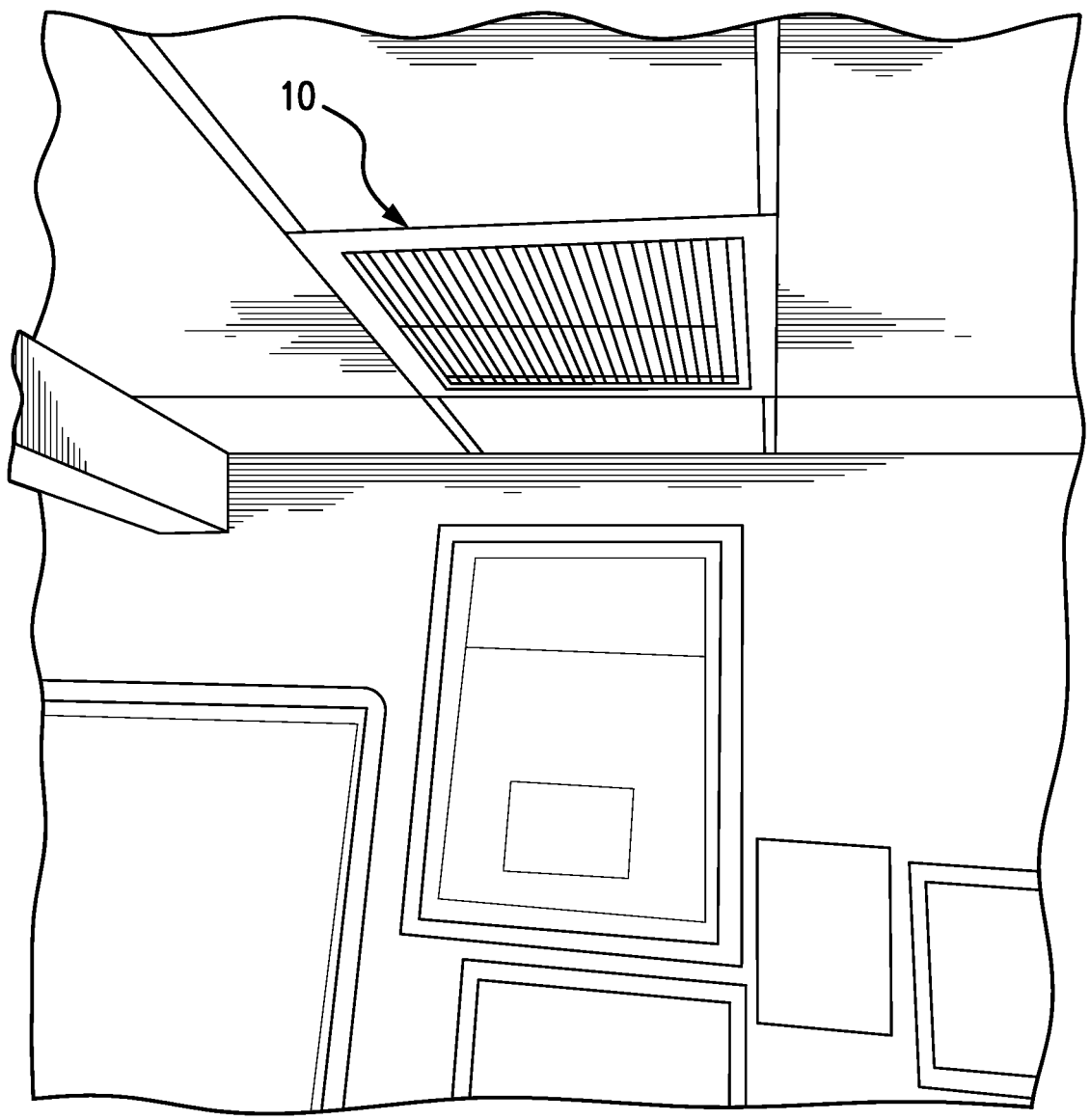

FIGS. 16 and 17 show the air filtration system 10 mounted in the return air space of a drop ceiling.

Figure 18:
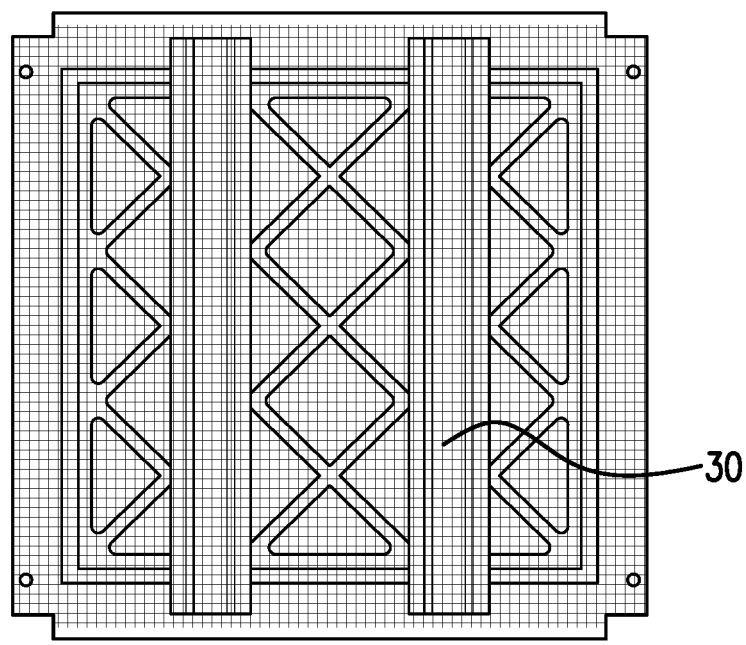
FIG. 18 shows the air filtration system 10 with the UV-C lamps 30 illuminated. This photo is from within the air plenum such that the ultraviolet light emanating from the lamps 30 does not substantially penetrate into the occupied space 16 (FIGS. 1A and 1B).

FIG. 18 shows the air filtration system 10 with the UV-C lamps 30 illuminated. This figure is from within the air plenum such that the ultraviolet light emanating from the lamps 30 does not substantially penetrate into the occupied space 16 (FIGS. 1A and 1B).

Figure 19:
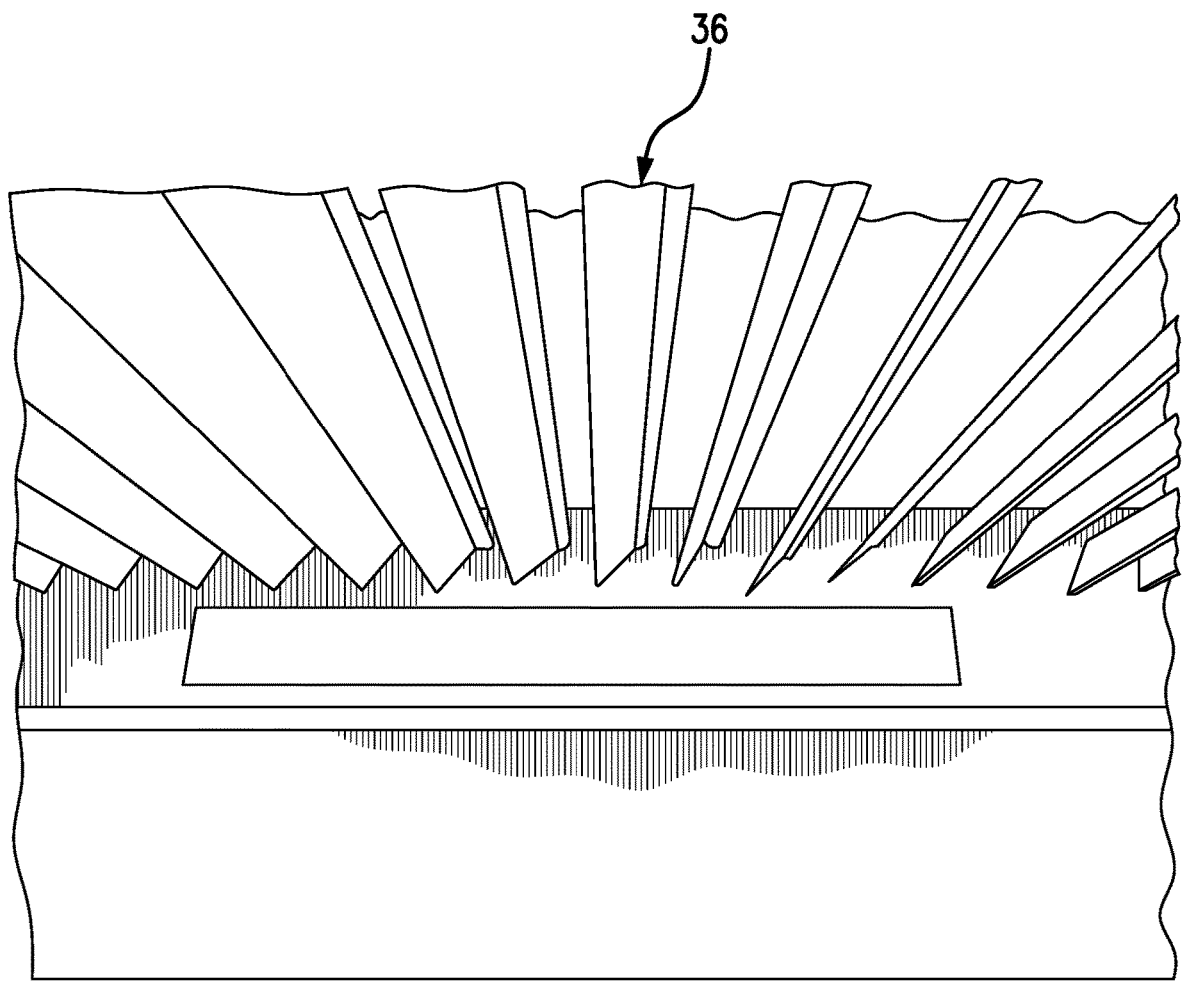
FIG. 19 illustrates a portion of the air filtration system, in particular the grille 36.

FIG. 19 illustrates a portion of the air filtration system, in particular the grille 36.

Figure 20:
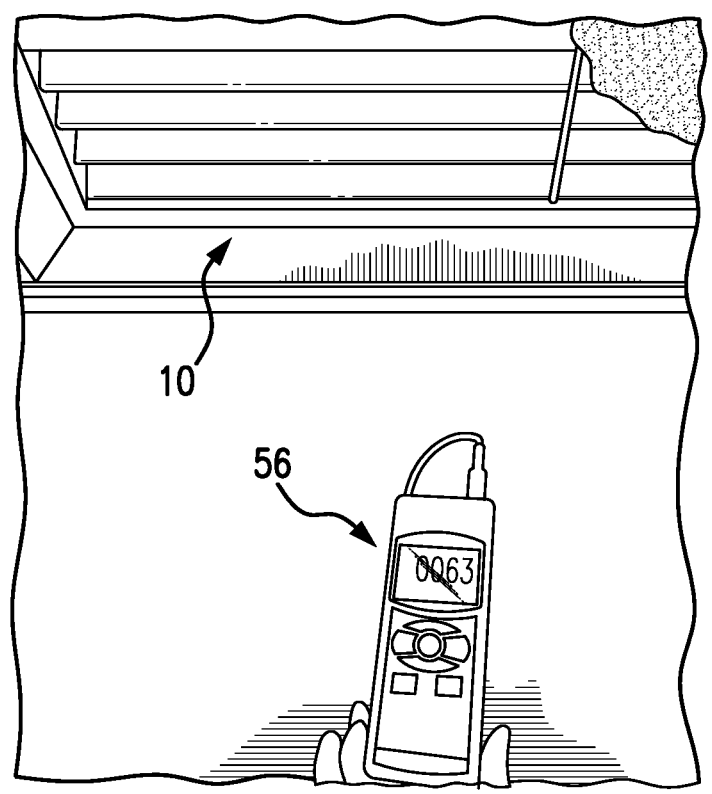
FIG. 20 shows the air filtration system 10 mounted within a drop ceiling and also illustrates that there is very low ultraviolet light emanating therefrom as shown by ultraviolet light meter 56.

FIG. 20 shows the air filtration system 10 mounted within a drop ceiling and also illustrates that there is very low ultraviolet light emanating therefrom as shown by ultraviolet light meter 56.

As seen in the above-identified drawings, the air filtration system 10 is arranged to filter and clean air passing therethrough so as to remove unwanted material including airborne particulates and in particular human generated respiratory droplets or droplet nuclei that are predominantly 1 µm in size and larger, as well as on-the-fly inactivation of microorganisms from entering the return air stream that is, from the occupied space into the air plenum.

The air filtration system 10 has an extrusion 40 that forms a frame to mount the system in a drop ceiling 12. The system has a pleated particulate air filter 38 that keeps the filter face velocity and the media velocity roughly the same, while the increased surface area of the pleated filter reduces the velocity of the airflow through the filter media, allowing increased collection efficiency.

The particulate filter collects the particles in three ways; impaction which occurs when a particle travels in the air stream and passes around a filter fiber, and deviates from the air stream (due to particle inertia) so as to collide with a fiber. It also includes interception which occurs when a large particle, because of its size, collides with a fiber in the filter that the air stream is passing through. It also filters by diffusion which occurs when the random (i.e., Brownian) motion of a particle causes that particle to contact a fiber. The filter is rated at MERV-13 and has been tested to remove capturing particles in 1 µm to 3 µm size range. This capture is at least 85% efficient.

The UV-C lamp 30 is a germicidal ultraviolet lamp and is used as an additional control to interrupt the transmission of pathogenic microorganisms. As seen in the figures, the design and placement is integral to the overall air filtration system with its the location in the fixture so as to allow for the highest possible UV-C dose rate due to it being at the point where the filtered air leaves the conditioned air/occupied space 16 (see FIGS. 1A and 1B). It is at this point that the air velocity and volume within the air filtration system are at their lowest and therefore provides for the highest possible UV-C dose rate capable by the air filtration system.

The UV-C lamps due to their ultraviolet irradiation of the air is able to destroy microorganisms/germs transmitted in aerosolized form. Microorganisms are generally less than 0.3 microns in diameter and are suspended or "float" in the air, and if they pass through the pleated particulate air filter and the UV-C lamp, a reduction in the total number of viable pathogenic microorganisms is greatly reduced in the airstream thus allowing the return air to the air plenum to be highly diminished in the amount of such microorganisms.

As shown in FIGS. 1B and 1B, the air filtration system 10 is placed within an occupied space where airborne particulates may exist such as human generated respiratory droplets and droplet nuclei. The arrangement of the components of the air filtration system with respect to the occupied space 16 avoids UV-C radiation within the occupied space to a great extent.

In an embodiment of the invention, the air moves through the air filtration system at a maximum velocity of 400-1000 cubic feet per minute and passes into a typical 24 inch by 24 or 48 inch extruded aluminum frame with duct mounting holes and through a 20 inch by 20 or 40 inch fixed bar grille 38, into the pleated MERV-13 filter 38 so as to remove particles and block the UV-C light from being projected into the occupied space.

The UV-C lamps 30 use germicidal fluorescent bulbs that are permanently connected at their base and have end connectors that plug into a pair of interconnected sockets. The typical "germicidal" UV wavelength is 253.7 nm. The UV-C lamps are typically treated with an interior coating that prevents vacuum UV (that is, 200 nm and below) from being emanated from the lamp and thus eliminates ozone production.

As shown in the figures, the air filtration system 10 according to an embodiment of the invention can be controlled from within the occupied room by, for example, hard-wired switches, occupancy sensors, or by a remote control system and is determined by the installer, project engineer and/or the owner of the building. The air filtration system may include a safety switch which interrupts power to the UV-C lamps 30 upon opening of the grille to ensure worker safety.

The present invention utilizes the following methods, benefits and include test results as discussed below.

CONCLUSION

With proper engineering, installation, and maintenance, an air filtration system 10 according to the present invention can use UV-C lamps 30 that are placed safely in a filtered return air grill. These findings demonstrate that careful application of return air UV-C can be achieved without an increase in the incidence of the most common side effects of accidental UV-C overexposure. The data recorded by the applicant with the filter in place demonstrates through experimental trials at both locations that there were no detectable levels of UV-C light emitted into the occupied space.

The overall air filtration system 10 according to the present invention has achieved various improvements over other types of air filters including:
- Designed to be installed with or without a return air plenum 14
- Designed to be installed at each return location within the occupied space/conditioned space 16 to stop cross contamination
- Designed to protect occupant safety by using a grille and pleated filter that radiates 0.000 mw/cm$^2$ into the occupied space
- Designed to protect the workers servicing the system by shutting off the UV-C lamp upon opening of the grille via an integrated safety switch
- Designed to protect occupant and worker safety by using a UV-C Lamp that is treated with an interior coating that prevents any vacuum UV (200 nm and below) from being emitted from the lamp, thus eliminating ozone production
- Designed to aid in the removal human generated respiratory droplets and droplet nuclei prior to the air stream exiting the occupied space and entering the duct work and or plenum (which may be common to multiple rooms IE potential for cross contamination)

The overall invention provides for an air filtration system that is able to effectively filter air from an occupied space so as to filter that air to prevent cross-contamination with any other occupied spaces to which the air plenum system may be associated.

Appendices 1-7 are respectively directed to:
Appendix 1—Methods and Benefits
Appendix 2—Safety Concerns and Mitigation Strategy
Appendix 3—Method of Testing for UV-C and Results
Appendix 4—TESTING: UV-C FIXTURE MOUNTED ON THE RETURN AIR GRILLE INSTALLATION
Appendix 5—SAFETY CONSIDERATIONS FOR UV-C INSTALLATIONS
Appendix 6—UV-C READINGS FOR THE SAMPLE INSTALLATION OF AIR FILTRATION SYSTEM 10
Appendix 7—References

APPENDICES

Appendix 1

Methods and Benefits
In an existing building:
1. The existing fan coil units utilize a common plenum return. Therefore, it would require a major above ceiling renovation to mount UV-C lights at each fan coil unit, including the installation of new return plenums, reconfiguration of the service access areas and would require that the ceiling tiles be removed yearly so the UV-C bulbs can be replaced.

2. Installation of the air filtration system is efficient and cost effective and requires no additional ductwork or electrical work. It is simply the removal of the existing return grills and installing the UV-C equipped filtered return air grill and plugging it into the existing fan coils convince outlet.

3. For ease and efficiency of service the UV-C bulb 30 and air filter 38 replacement can be achieved without removing the ceiling tiles, entering the plenum and does not require any tools.

4. The filter section of the return grill will be equipped with a 20×20×1 high efficiency filter with a rating of 13 Minimum Efficiency Reporting Value (MERV). This will provide between 85% and 90% efficiency for particles between 3 and 10 microns in size including mold spores, 65% and 80% for particles between 1 and 3 microns in size including legionella, 20% and 35% efficiency for particles between 0.30 and 1 micron in size including bacteria, most smoke, sneeze nuclei, copier toner, and face powders.

5. The UVGI light location is strategic and provides sufficient contact time to attack airborne viruses in return air stream. The light's intensity is based on the volume of air to maximize disinfection rate microbial agents. Federal Agencies including OSHA, NIOSH and the CDC use the term UVGI when directly referring to the process of killing surface and airborne microorganisms.

6. To maximize airflow and aid in the removal of the infectious aerosols the UV-C equipped filtered return air grill will be installed so the air is drawn up and away from walkways and the occupant's desk areas.

7. The UV-C fixture incorporates a switch located above the air filter so the fixture will be turned off automatically when the filter is removed.

Appendix 2

Safety Concerns and Mitigation Strategy

UV-C Lamps safety concerns; Ozone, Skin, Eye irritation and environmental impacts that we addressed and verified through an experimental trial. Below is a brief explanation and the engineering controls that will implemented to reduce any exposure risks.

1. Ozone may be generated during this process; we selected bulbs that do not create ozone.

2. Skin irritation from exposure to UV-C; we chose to place the lamps in the ceiling above a filtered return grill.

3. Eye irritation from exposure to UV-C; again, this is eliminated by placing them directly above a filtered return grill.

4. All UV-C lamps use mercury; the UV-C bulbs we selected utilize less than 5.5 mg of mercury per lamp compared to quartz UV-C lamps, which can exceed 100 mg of mercury. These bulbs are recycled with along with fluorescent light bulbs and require no special handling procedures.

Appendix 3

Method of Testing for UV-C and Results

We have strategically placed the UV-C equipped filtered return air grill in such a way as to maximize airflow upward toward the return air grill from the walkways and away from the occupants' desk areas. The collection of exposure level data involved taking readings of the UV-C light levels at the ceiling and down to 30 inches from the floor at two locations within an open office space. Below are the results of our readings under the 3 possible conditions that can occur during operation and maintenance of the UV-C equipped filtered return air grill.

1. Return grill with a filter installed; we recorded readings of 0.0 µW/cm2 at 8 feet above the floor and this is well below the 0.2 µW/cm2 permissible limit of irradiance at eye height.

2. Return grill with the filter removed; at 8 feet above the floor we observed readings that ranged from 0.059-0.043 µW/cm2 and at 6 feet above the floor we observed 0.00 mW/cm2.

3. Return grill with filter removed and the filter access left open; at 8 feet above the floor we observed a maximum reading of 0.802 µW/cm2 and at 6 feet above the floor we observed a maximum reading was 0.153 µW/cm2.

All of the observed readings at 6 feet and below were less than the TLV of 0.2 µW/cm2 permissible limit of irradiance at eye height.

Appendix 4

Testing: UV-C Fixture Mounted on the Return Air Grille Installation

We installed 2 Ceiling return grills with 1" pleated MERV 8 filters and UV-C lights in the ceiling of the open office space and powered them from the existing fan coil units 110 VAC axillary power outlets. The UV-C lights in the 1st fixture are 14" 18 Watt bulbs (2×) and produce 6.0 mJ/cm2 at their surface with an intensity of 1179 @12" the 2nd fixture are 17" 20 Watt bulbs (2×) and produce 6.0 mJ/cm2 at their surface with an intensity of 1905 @12".

Two grills have been placed in the existing ceiling grid over the common walkway to aid in providing an airflow pattern away from the last trading desk in each row. The airflow based on the fan coil units is 230 CFM maximum at each grill and there is a total of 33 return air grills.

Appendix 5

Safety Considerations for UV-C Installations

Highly active photochemical, 254 nm UV would be expected to be more damaging to exposed skin and eyes than longer wavelengths, such as UV-A and UV-B, in sunlight. However, 254 nm UV is so completely absorbed by chromophores in the outer dead layer of skin that it is estimated that only 5% of 254 nm UV at the skin surface penetrates to the top viable cell layer, compared with 15% for 365 nm (UV-A) and 50% for 297 nm (UV-B).1

The American Conference of Governmental Industrial Hygienists (ACGIH) Committee on Physical Agents has established a Threshold Limit Value (TLV) for UV-C exposure to avoid such skin and eye injuries among those most susceptible. For 254 nm UV, this TLV is 6 mJ/cm2 over an eight-hour period. The TLV function differs by wavelengths because of variable energy and potential for cell damage. This TLV is supported by the International Commission on Non-Ionizing Radiation Protection3 and is used in setting lamp safety standards by the Illuminating Engineering Society of North America.4 Until quite recently, this TLV was interpreted as if eye exposure in rooms was continuous over eight hours and at the highest eye-level irradiance found in the room. In those highly unlikely conditions, a 6.0 mJ/cm2 dose is reached under the ACGIH TLV after just eight hours of continuous exposure to an irradiance of 0.2 µW/cm2.

Thus, 0.2 μW/cm2 is widely interpreted as the upper permissible limit of irradiance at eye height.

In an accidental exposer that was reported in 2006 and occurred in Italy, twenty-six medical students were exposed to a bare-bulb direct (lower-room) germicidal UV source for 90 minutes during an autopsy demonstration.5 A timer that was intended to disinfect the area at night when the suite was unoccupied had malfunctioned. All subjects reported both eye and skin symptoms. Although the calculated absorbed irradiation was approximately 700 mJ/cm2, based on meter measurements, the effective irradiance according to skin phototype and symptoms was far less—between 50 and 100 mJ/cm2. This finding supports UV monitoring data by First and colleagues that peak meter readings poorly predict actual exposure of room occupants. Despite UV-C exposure 20 to 100 times higher than the TLV, all but one student had complete resolution of skin symptoms within two weeks of the incident. Ocular symptoms lasted two to four days, with no residual findings.

Appendix 6

UV-C Readings for the Sample Installation of Air Filtration System 10

We placed the meter on an 8' ladder at the top, on the 2nd step from the top at 6' and on the file cabinet and observed the following readings.

| Meter Location Distance from the Floor | Minimum | Maximum | Mean | Notes |
|---|---|---|---|---|
| 8' | 0.00 mW/cm2 | 0.00 mW/cm2 | 0.00 mW/cm2 | Grill with Filter Installed |
| 6' | 0.00 mW/cm2 | 0.00 mW/cm2 | 0.00 mW/cm2 | |
| 30" | 0.00 mW/cm2 | 0.00 mW/cm2 | 0.00 mW/cm2 | Reading at file cabinet |
| 8' | 0.043 mW/cm2 | 0.059 mW/cm2 | 0.051 mW/cm2 | Grill with Filter removed |
| 6' | 0.00 mW/cm2 | 0.00 mW/cm2 | 0.00 mW/cm2 | |
| 30" | 0.00 mW/cm2 | 0.00 mW/cm2 | 0.00 mW/cm2 | Reading at file cabinet |
| 8' | 0.555 mW/cm2 | 0.802 mW/cm2 | 0.678 mW/cm2 | Grill with open & no filter |
| 6' | 0.305 mW/cm2 | 0.378 mW/cm2 | 0.341 mW/cm2 | |
| 30" | 0.00 mW/cm2 | 0.00 mW/cm2 | 0 mW/cm2 | Reading at file cabinet |

UVC Lamp Calculation for Return Air Grills

| Unit | Return Duct | | | CFM | DF | (V) FPM | Lamp # or Code |
|---|---|---|---|---|---|---|---|
| | Width (inches) | Height (inches) | Length (ft.) | | | | |
| Typical Ceiling Rtn | 20 | 20 | 1 | 230 | 70 | 82.8 | TUV T5 |
| Typical Ceiling Rtn | 20 | 20 | 1 | 230 | 70 | 82.8 | 16T TG |
| Dose (in μW) = | 2005 | | | | | | |

| UVC Intensity μW/cm$^2$ @1mUV Output | # lamps | Duct sq. ft. | Kill zone volume (cu. ft.) | Exposer Time (s) | Intensity required | Lamp Intensity @ Temp |
|---|---|---|---|---|---|---|
| 758 | 2.3 | 2.78 | 2.78 | 0.72 | 2766.90 | 1179.11 |
| 1225 | 1.5 | 2.78 | 2.78 | 0.72 | 2766.90 | 1905.56 |

| Based on the datasheet information from USHIO UV bulbs [1]: | Units: |
|---|---|
| A G15T8 (15 W germicidal fluorescent bulb) emits 4.9 W of UV-C with a central peak at 253.7 nm | UV_Energy: Joules |
| The UV dose is UV_Energy/Area | UV_bulb_power: Watts |
| UV_Energy = UV_bulb_power * Exposure_time | Area: m^2 |
| Area = 4* pi * (UV_bulb distance)^2 (considering spheric diverence) | UV_bulb_distance: m |
| This leads to: | Exposure_time: s |
| UV_Energy = UV_bulb_power * Exposure_time/ (4 * pi * UV_bulb_distance^2) | pi: 3.141592 |
| So the desired direct exposure time in seconds is: | So for the desired 5 J/m^2 Energy we got |
| Exposure_time = (Desired_UV_Energy * 4 * pi * (UV_bulb_distance)^2)/UV_bulb_power | 12.8 seconds of direct exposure for a 1 m distance |

Appendix 7

References

1. Bruls W A, Slaper H, van der Leun J C, Berrens L. Transmission of human epidermis and stratum corneum as a function of thickness in the ultraviolet and visible wavelengths. Photochem Photobiol. 1984; 40:485-94. [PubMed]
2. American Conference of Governmental Industrial Hygienists. TLVs and BEls. Cincinnati: ACGIH; 1999. [Google Scholar]
3. International Commission on Non-Ionizing Radiation Protection. Guidelines on UV radiation exposure limits. Health Phys. 1996; 71:978. [PubMed]
4. Illuminating Engineering Society of North America. RP-27.2-00. IESNA Photobiology Committee. Recommended practice for photobiological safety for lamps and lamp systems—measurement systems, techniques. New York: IESNA; 2000. [Google Scholar]
5. Trevisan A, Piovesan S, Leonardi A, Bertocco M, Nicolosi P, Pelizzo M G, et al. Unusual high exposure to ultraviolet-C radiation. Photochem Photobiol. 2006; 82:1077-9. [PubMed]
6. First M W, Weker R A, Yasui S, Nardell E A. Monitoring human exposures to upper-room germicidal ultraviolet irradiation. J Occup Environ Hyg. 2005; 2:285-92. [PubMed]

The threshold limit value (TLV) of a chemical substance is believed to be a level to which a worker can be exposed day after day for a working lifetime without adverse effects. Strictly speaking, TLV is a reserved term of the American Conference of Governmental Industrial Hygienists (ACGIH). TLVs issued by the ACGIH are the most widely accepted occupational exposure limits in the United States.

ASHRAE Standard 52.2-1999 measures particle size efficiency (PSE). This newer standard is a more descriptive test, which quantifies filtration efficiency in different particle size ranges for a clean and incrementally loaded filter to provide a composite efficiency value. It gives a better determination of a filter's effectiveness to capture solid particulate as opposed to liquid aerosols. The 1999 standard rates particle-size efficiency results as a MERV between 1 and 20. A higher MERV indicates a more efficient filter. In addition, Standard 52.2 provides a table (see Table 1) showing minimum PSE in three size ranges for each of the MERV numbers, 1 through 16. Thus, if you know the size of your contaminant, you can identify an appropriate filter that has the desired PSE for that particular particle size.

Pathogenic Microorganisms, such as *Mycobacterium tuberculosis*(TB), influenza viruses, mold, and potential bioterrorism agents (Brickner et al. 2003; CDC 2002, 2005; GSA 2010; McDeVitt et al. 2008; Rudnick et al. 2009). Brickner, P. W., R. L. Vincent, M. First, E. Nardell, M. Murray, and W. Kaufman. 2003. The application of ultraviolet germicidal irradiation to control transmission of airborne disease: Bioterrorism countermeasure. Public Health Report 118(2):99-114. CDC. 2002. Comprehensive procedures for collecting environmental samples for culturing *Bacillus anthracis*. Centers for Disease Control and Prevention, Atlanta. www.cdc.gov/niosh/topics/emres/unp-envsamp.html. CDC. 2005. Guidelines for preventing the transmission of *Mycobacterium tuberculosis* in health-care settings. Morbidity and Mortality Weekly Report (MMWR) 37-38, 70-75. McDevitt, J. J., D. K. Milton, S. N. Rudnick, and M. W. First. 2008. Inactivation of poxviruses by upper-room UV-C light in a simulated hospital room environment. PLoS ONE3(9):e3186.journals.plos.org/plosone/article?id=10.1371/journal.pone.0003186.

Environmental controls include methods to reduce the concentration of infectious respiratory aerosols (i.e. droplet nuclei) in the air, and methods to control the direction of infectious air. The choice of environmental controls is intimately related to building design, construction, renovation and use, which in turn must be tailored to local climatic and socioeconomic conditions. Environmental controls include: ventilation (natural, mechanical and mixed-mode) to dilute concentrations of organisms and exhaust them outside; filtration to capture infectious particles; and germicidal ultraviolet (GUV) with air-mixing systems (previously known as ultraviolet germicidal irradiation, [UVGI], which inactivate these airborne organisms as they pass through the irradiated upper room of occupied spaces and disinfected air returns to the occupied zone. GUV compliments building ventilation, both mechanical and natural, but can also be the main means of air disinfection where mechanical ventilation is absent or functions poorly, and natural ventilation is limited.

Maintenance Manual Focus: The focus of this manual is to describe what is necessary to sustainably maintain an UV-C system. Maintenance is defined as actions necessary for retaining or restoring a piece of equipment, machine, or system to the specified operable condition to achieve its maximum useful performance. Further it includes corrective (reactive) maintenance and preventive maintenance. Reactive maintenance covers immediate action necessary to troubleshoot a system failure, (e.g., a light burns out and needs replacement or the light flickers and needs a new ballast) and in response to reports on possible occupant overexposure in the occupied zone. Preventive maintenance is a systematic, scheduled review of the equipment with regular cleaning and replacement of parts at the end of useful life and measurement of output and safe operation.

UV-C: ultraviolet radiation with a wavelength between 280 nm and 100 nm. The "germicidal" UV wavelength (commonly 253.7 nm when generated using a florescent low-pressure mercury vapor lamp). It is desirable to effect air sterilization within the room where the germs originate. However, there are safety issues. Keratoconjunctivitis (external idammation of the eye) and erythmea (reddening of the skin) can result from overexposure National Institutes for Occupational Safety and Health (NIOSH) recommends an upper limit on the amount of W-C radiation for the safety of personnel in the room, i.e., 6 pJ/cm2-6 micro-joules per square centimeter over a continuous eight-hour period.

The UV-C lights are treated with an interior coating that prevents any vacuum UV (200 nm and below) from being emitted from the lamp, so ozone production is not an issue. Poor quality UV-C lamps will produce ozone. Replacement UV-C lamps need to be non-ozone producing. Recycling of used UV-C lamps should comply with national and local environmental regulations based on manufacturer's documentation of mercury content within their UV-C lamps.

The UV-C lights should be cleaned regularly and replaced when their output decreases by 20%.

UL Standard 1995-89.2 89.2.1-2

2 89.2.1 For the occupied space area outside the unit a test shall be performed to determine the UV-C irradiance. The emissions from the equipment shall not exceed a UV-C irradiance of 0.1 μW/cm2 based on a TLV of 6.0 mJ/cm2 at 254 nm as defined in the ACGIH standard. The ultraviolet (UV) emissions are measured at the nearest point of accessibility.

89.2.2 For areas inside the unit that do not contain the ultraviolet (UV) lamp system, but are accessible for anticipated servicing and cleaning there shall be no UV-C irradiance greater than 1.7 µW/cm2 based on a TLV of 6.0 mJ/cm2 at 254 nm as defined in the ACGIH standard. The ultraviolet (UV-C) emissions are measured at any point of anticipated serviceman accessibility within the service area. When determining serviceman accessibility, consideration should be given to the actual degree of exposure that the serviceman would experience in performing his duties.

What is claimed is:

1. An air filtration system comprising:
   an occupied space from which air is taken in;
   an air plenum from which air is returned to the occupied space;
   an extruded frame with an associated grille proximal to the occupied space, the extruded frame configured to be inserted within a structure associated with the air plenum, the structure being a drop ceiling, a solid ceiling or a wall separating the occupied space from the air plenum;
   a pleated filter positioned adjacent the grille, the pleated filter dimensioned for entrapping particles in the 1 to 3 micron size,
   an ultraviolet lamp for emitting UV-C light positioned adjacent the pleated air filter so as to irradiate airborne particles that may pass through the pleated filter prior to flowing into the air plenum from the occupied space, and in particular to irradiate particles associated with microorganisms, including viruses,
   an electrical switch and associated electrical ballast for controlling operation of the electrical lamp and so as to ensure that the lamp is not energized when the air filtration system is being installed or service; and
   means for securing the extruded frame of the air filtration system to the structure;
   wherein the grille, the pleated filter, and the ultraviolet lamp form proximal and parallel layers between the occupied space and the return air duct.

2. The air filtration system according to claim 1, wherein the ultraviolet lamp is positioned in a spaced relationship to the pleated air filter so as to provide irradiation of airborne microorganisms including airborne viruses.

3. The air filtration system according to claim 1, wherein airflow through the air filtration system provides air going into the air plenum from the occupied space.

4. The air filtration system according to claim 1, wherein the frame and associated electrical connectors of the ultraviolet lamp can be installed within a drop ceiling or solid ceiling or wall without additional duct work or electrical elements.

5. The air filtration system according to claim 1, wherein a filter section associated with the grille is equipped with a 20×20×1 inch high-efficiency pleated filter with a rating of 13 Minimum Efficiency Reporting Value (MERV).

6. The air filtration system according to claim 1, wherein mounting options for the air filtration system include a solid wall or ceiling, and in a drop ceiling grid, include prelude, interlude, silhouette or a superfine interfacing with ceiling grid clips.

7. The air filtration system according to claim 1, including a recessed mounting kit for installation in drywall ceilings or walls of a building.

8. The air filtration system according to claim 7, wherein the mounting kit forms a square frame.

9. The air filtration system according to claim 8, wherein the square frame is 2 feet on all sides.

10. The air filtration system according to claim 1, wherein the air filtration system is configured for a plenum installation.

11. The air filtration system according to claim 1, wherein the air filtration system is configured for a ducted return installation.

12. The air filtration system according to claim 1, wherein the extruded frame is a one-piece extrusion.

* * * * *